(12) United States Patent  
Takae et al.

(10) Patent No.: US 8,376,612 B2
(45) Date of Patent: Feb. 19, 2013

(54) MOBILE X-RAY APPARATUS

(75) Inventors: Tomokazu Takae, Tokyo (JP); Yuji Oda, Tokyo (JP); Koichiro Oku, Tokyo (JP); Shinya Kitamura, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 265 days.

(21) Appl. No.: 12/918,627

(22) PCT Filed: Feb. 19, 2009

(86) PCT No.: PCT/JP2009/052828
§ 371 (c)(1),
(2), (4) Date: Aug. 20, 2010

(87) PCT Pub. No.: WO2009/104656
PCT Pub. Date: Aug. 27, 2009

(65) Prior Publication Data
US 2010/0329427 A1 Dec. 30, 2010

(30) Foreign Application Priority Data

Feb. 22, 2008 (JP) .................................. 2008-040748

(51) Int. Cl.
*H05G 1/02* (2006.01)
(52) U.S. Cl. ...................................................... 378/198
(58) Field of Classification Search .......... 378/114–117, 378/198
See application file for complete search history.

(56) References Cited

U.S. PATENT DOCUMENTS

2008/0025469 A1*   1/2008   Watanabe ..................... 378/198

FOREIGN PATENT DOCUMENTS

| JP | 4-190224 | 7/1992 |
| JP | 9-299359 | 11/1997 |
| JP | 2004-184905 | 7/2004 |
| JP | 2005-003755 | 1/2005 |
| JP | 2006-043273 | 2/2006 |
| JP | 2008-076585 | 4/2008 |

* cited by examiner

*Primary Examiner* — Courtney Thomas
(74) *Attorney, Agent, or Firm* — Brundidge & Stanger, P.C.

(57) ABSTRACT

A mobile X-ray apparatus including a main body portion, a mobile dolly on which the main body portion is mounted, a support pole that is erectly provided on the mobile dolly, an X-ray generator supported on the support pole, and an image reading device for reading image information from an imaging plate in which X-ray image information is stored, and further including detecting means for detecting whether the mobile dolly is being moved, and reading control means for prohibiting reading of the image reading device when it is detected by the detecting means that the mobile dolly is being moved.

6 Claims, 3 Drawing Sheets

MOBILE X-RAY APPARATUS

TECHNICAL FIELD

The present invention relates to a mobile X-ray apparatus that is movable in a hospital to perform X-ray imaging in a hospital room or the like. Particularly, the present invention relates to a mobile X-ray apparatus that can immediately check an X-ray image picked up by using an imaging plate (IP) at an image pickup place.

BACKGROUND ART

Needs for picking up images of patients who are difficult to move from hospital rooms, urgently picking up images in an operating room, etc. have recently increased in medical fields, and a mobile X-ray apparatus which is movable to a hospital room or the like to perform X-ray imaging has been broadly popular. Recently, a mobile X-ray apparatus having an image reading device for reading image information from IP is being put into practical use so that a picked up X-ray image is immediately checked at an image pickup place to determine at that place whether re-imaging is required or not.

For example, Patent Document 1 discloses an X-ray apparatus for doctor's round visits which is equipped with an image information reading device for reading image information accumulated in IP. According to this X-ray apparatus for doctor's round visits, image information read out by the image information reading device is transmitted to a CRT display fixed on a top surface of a main body to display an X-ray image.

The image reading device scans a laser beam in a main scan direction (a direction perpendicular to an auxiliary scan direction) while feeding IP in the auxiliary scan direction to successively scan the whole IP surface and detect photostimulable emission light at each point, thereby reading image information. In order to obtain an accurate image, it is important to perform the feeding of IP and the laser scanning accurately with high precision, and it is not preferable that vibration, impact or inclination is applied when image information is read.

Patent Document 1: JP-A-4-190224

DISCLOSURE OF THE INVENTION

Problem to be Solved by the Invention

However, it is possible in the conventional mobile X-ray apparatus to insert a cassette having IP mounted therein into an image reading device and read image information from IP which has been subjected to image pickup even when a mobile dolly is moving. Therefore, when an operator makes the image reading device read image information during movement of the mobile X-ray apparatus, there is a case where the read-out image information may be damaged due to vibration or impact occurring due to the movement and thus an accurate image cannot be obtained.

The present invention has been implemented in view of the foregoing situation, and has an object to provide a mobile X-ray apparatus that can reduce a risk that image formation being read out by the image reading device is damaged.

Means of Solving the Problem

A mobile X-ray apparatus according to the present invention comprises a main body portion, a mobile dolly on which the main body portion is mounted, a support pole that is erectly provided on the mobile dolly, an X-ray generator supported on the support pole, and an image reading device for reading image information from an imaging plate in which X-ray image information is stored, and is characterized by further comprising detecting means for detecting whether the mobile dolly is being moved, and reading control means for prohibiting reading of the image reading device when it is detected by the detecting means that the mobile dolly is being moved.

Effect of the Invention

According to the mobile X-ray apparatus of the present invention, when the mobile dolly is being moved, the image reading device cannot read image information, and thus a risk that image information read out from IP is damaged due to vibration or impact can be reduced. Furthermore, according to the mobile X-ray apparatus of the present invention, a risk that IP from which image information is being read out comes into contact with each kind of part in the image reading device due to vibration or impact can be reduced.

DESCRIPTION OF REFERENCE NUMERALS

M mobile X-ray apparatus, 1 main body portion, 11 operation panel, 12 handle, 13 brake release switch, 14 monitor, 2 mobile dolly, 21 front wheel, 22 rear wheel, 23 motor, 24 electromagnetic brake, 3 support mechanism, 31 support pole, 32 arm, 31r rotating mechanism, 33, 34 electromagnetic brake, 35 attitude sensor, 4 X-ray generator, X-ray tube, 42 X-ray movable aperture device, 43 knob, arm fixing release switch, 5 image reading device, 51 cassette insertion port, 52 lid, 53 cassette detection sensor, MC main controller, 100 motor control means, 101 brake control means, 102 irradiation control means, 103 support mechanism control means, 104 attitude determining means, 105 reading control means, 106 reading execution determining means, 107 opening/closing control means, 108a first display control means, 108b second display control means

MODES FOR CARRYING OUT THE INVENTION

Figure 1:
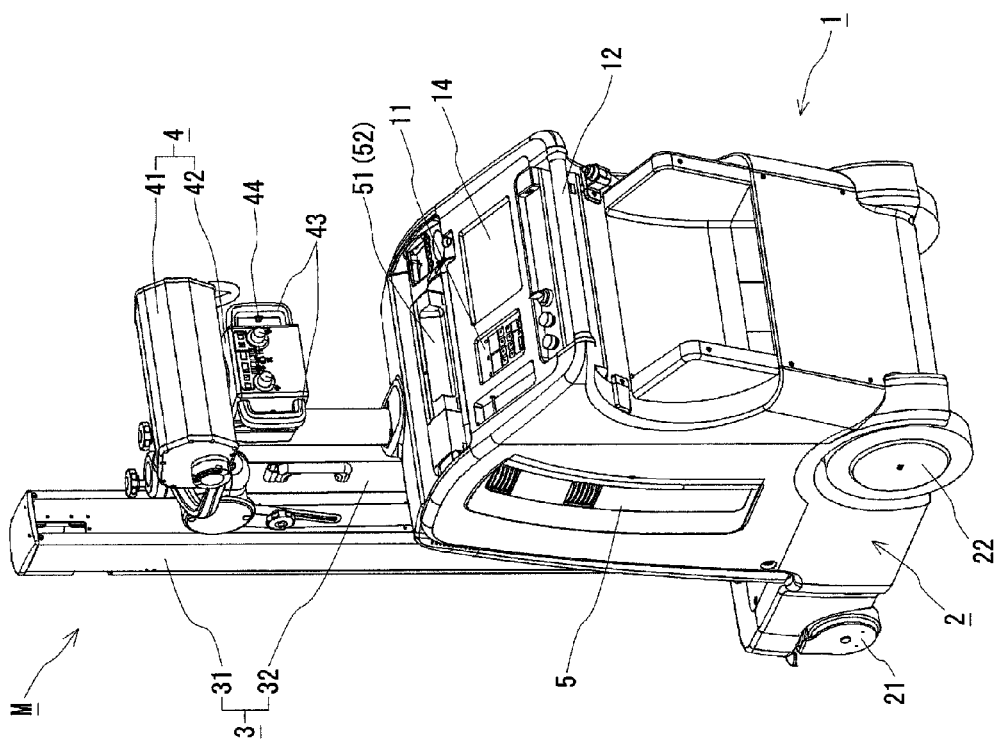
FIG. 1 is a perspective view of the back side of a mobile X-ray apparatus according to an embodiment.
Figure 2:
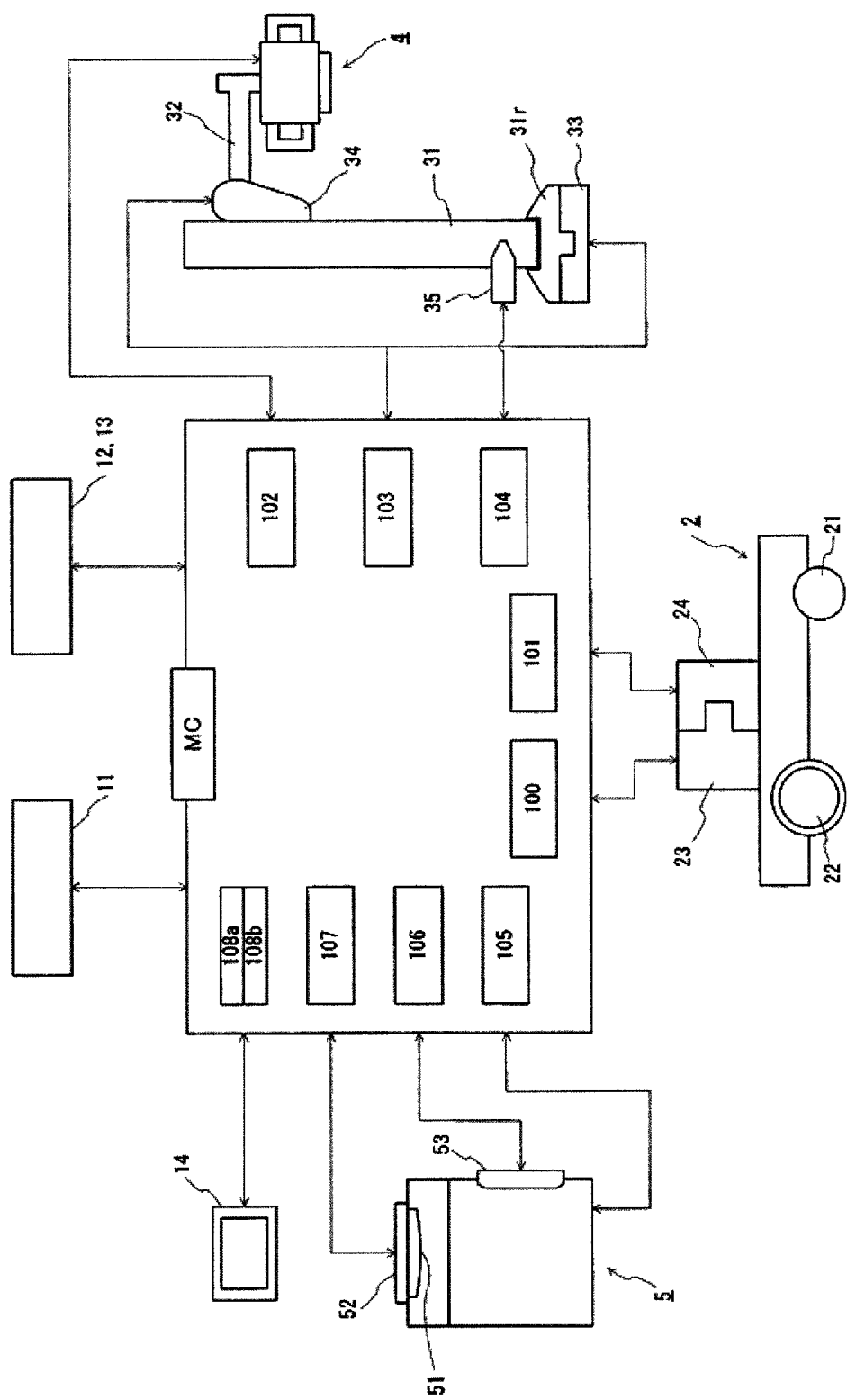
FIG. 2 is a functional block diagram showing a mobile X-ray apparatus according to the embodiment.

An embodiment of the present invention will be described with reference to the drawings. FIG. 1 is a perspective view showing a mobile X-ray apparatus according to an embodiment, and FIG. 2 is a functional block diagram showing the mobile X-ray apparatus.

[Construction of Mobile X-Ray Apparatus]

A mobile X-ray apparatus M of this invention has a main body portion 1, a mobile dolly 2, a support mechanism 3, an X-ray generator 4 and an image reading device 5 (FIG. 1). When X-ray imaging is executed, a cassette having IP mounted therein is used. Specifically, an image pickup target is disposed between the X-ray generator and the cassette (IP), X-ray is emitted from the X-ray generator, and X-ray transmitted through the image pickup target is stored in IP.

An operation panel 11, a handle 12 and a monitor 14 for operating various kinds of equipment and devices mounted in the mobile X-ray apparatus M are secured to the main body portion 1, and also a power source is mounted in the main body portion 1. Furthermore, a main controller MC is contained in the main body portion 1, and the main controller MC is connected to the various kinds of equipment and devices (FIG. 2). An arrow in FIG. 2 represents an input/output of a signal (data), and the various kinds of equipment and devices are operated in accordance with signals from the main controller MC.

The mobile dolly 2 has pairs of right and left front wheels 21 and rear wheels 22. The front wheels 21 are freely turnable casters, and the rear wheels 22 are driving wheels which are driven by a motor 23 mounted in the mobile dolly 2. The motor 23 is rotatable forwardly and reversely, and transmits the rotation of the output shaft thereof to the rear wheels 22 to drive (rotate) the rear wheels 22. An electromagnetic brake is secured to the output shaft of the motor 23. The electromagnetic brake 24 is a non-excitation-operated electromagnetic brake. Under a de-energization state, the brake is actuated to induce braking force to the output shaft, thereby braking (stopping) the rear wheels 22.

When the mobile dolly 2 (mobile X-ray apparatus M) is moved, an operator grips and manipulates the handle 12. The handle 12 is provided with a brake release switch 13. The electromagnetic brake 24 is energized to release the brake while the switch 13 is pushed. Furthermore, energization to the electromagnetic brake 24 is interrupted to actuate the brake while the switch 13 is released. Therefore, when the mobile dolly 2 is moved, the operator grips and manipulates the handle 12 so as to push the brake release switch 13. Electrical sensors such as potentiometers or the like are installed at both the end portions of the handle 12, and when the handle 12 is pushed forwardly, the motor 23 rotates forwardly, and the mobile dolly 2 goes ahead. When the handle 12 is pulled backwardly, the motor 23 rotates reversely, and the mobile dolly 2 goes back. The main controller MC can determine through the electrical sensor whether the mobile dolly 2 goes ahead or back, and thus it functions as detecting means for detecting whether the mobile dolly 2 is being moved.

As not shown, a rotary encoder may be added to the wheel shaft of the mobile dolly 2 so that it may be made to function as detecting means for detecting whether the mobile dolly 2 is being moved. That is, the detecting means may contain any means and method insofar as it can detect that the mobile dolly 2 is being moved.

When the mobile dolly 2 is braked (stopped), the operator returns the handle 12 to the intermediate position, and also releases the bake release switch 13, whereby energization to the motor 23 and the electromagnetic brake 24 is interrupted, and rotation of the motor is stopped, whereby the brake is actuated. The driving or stop of the motor 22 is executed by motor control means 100 stored in the main controller MC, and the actuation or release of the electromagnetic brake 23 is executed by brake control means 101 stored in the main controller MC.

The support mechanism 3 is a mechanism for supporting the X-ray generator 4, and has a support pole 31 and an arm 32. The support pole 31 is erected on the mobile dolly 2, and a rotating mechanism 31r which is freely rotated around its axis and an electromagnetic brake 33 for braking the rotation of the support pole are secured to the fixing place of the support pole 31 to the mobile dolly 2. The arm 32 is secured to the support pole 31 so as to be freely moved upward and downward, and the electromagnetic brake 34 for braking the upward and downward movement of the arm 32 is secured to the fixing place of the arm 32 to the support pole 31. These electromagnetic brakes 33 and 34 are non-excitation operated electromagnetic brakes, and under the de-energization state, the brake is actuated, and the rotational angle of the support pole 31 and the up/down movement position of the arm 32 are fixed. The X-ray generator 4 is secured to the tip portion of the arm 32. A movement detecting sensor such as a rotary encoder or the like for detecting the rotational state or the movement state may be secured to the rotating mechanism 31r and an up/down movement mechanism for the arm 32, whereby it is detected whether the support pole 31 or the arm 32 is being moved.

The X-ray generator 4 is supported by the support pole 31 through the arm 32. The X-ray generator 4 has an X-ray tube 41 for generating X-ray, and an X-ray movable aperture device 42 is secured to the X-ray irradiation port. Irradiation control means 102 for permitting or prohibiting X-ray irradiation of the X-ray generator 4 is stored in the main controller MC, and the X-ray generator 4 cannot emit X-ray when the irradiation control means 102 prohibits X-ray irradiation.

When the rotational angle of the support pole 31 or the up/down movement position of the arm 32 is adjusted to adjust the position of the X-ray generator 4, the operator grips and manipulates a knob 43 provided to the X-ray generator 4. The knob 43 is provided with an arm fixing release switch 44. Each of the electromagnetic brakes 33 and 34 is energized while the switch 44 is pushed, thereby releasing the brake. Furthermore, energization to each of the electromagnetic brakes 33 and 34 is interrupted while the switch 44 is released, thereby actuating the brake. Therefore, when the position of the X-ray generator 4 is adjusted, the operator grips and manipulates the arm fixing release switch 44 so as to push the arm fixing release switch 44. The operator adjusts the rotational angle of the support pole 31 and the up/down movement position of the arm 32 to position the X-ray generator 4, and then releases the arm fixing release switch 44, whereby the respective electromagnetic brakes 33 and 34 are actuated and the rotational angle of the support pole 31 and the up/down movement position of the arm 32 are fixed. The actuation or release of each of the electromagnetic brakes 33 and 34 is executed by support mechanism control means 103 stored in the main controller MC.

Figure 3:
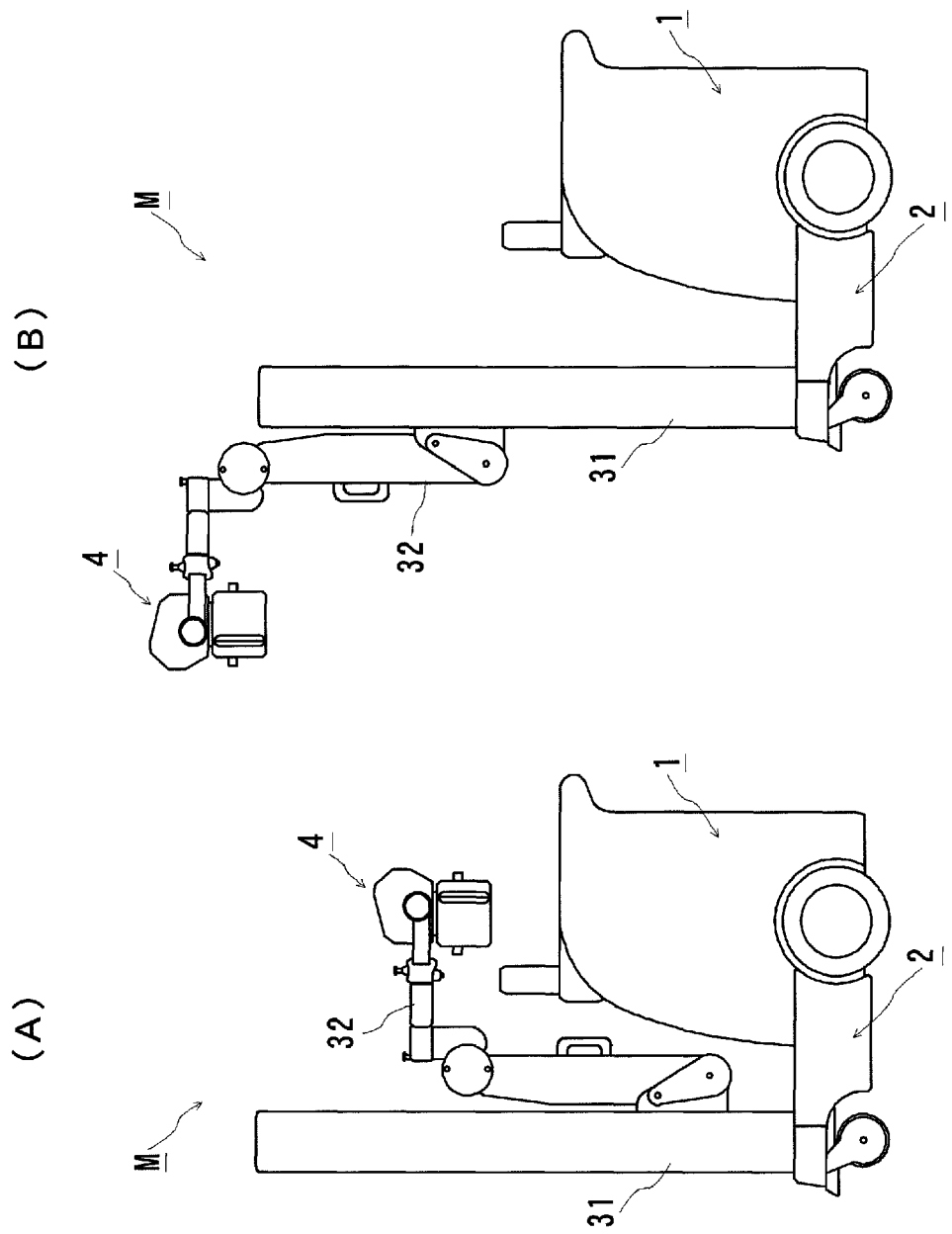
FIG. 3(A) is a schematic diagram showing a movement attitude of the mobile X-ray apparatus according to the embodiment, and (B) is a schematic diagram showing an imaging attitude of the mobile X-ray apparatus according to the embodiment.

The mobile X-ray apparatus M rotates the support pole 31 around its axis to turn the arm 32 around the axis of the support pole 31, whereby a moving attitude (FIG. 3(A)) under which the X-ray generator 4 is located above the main body portion 1 (mobile dolly 2) and an imaging attitude (FIG. 3(B)) under which the X-ray generator 4 protrudes from the main body portion 1 (mobile dolly 2) can be switched to each other. An attitude sensor 35 for detecting the rotational angle of the support pole is secured to the bottom portion of the support pole 31, and attitude determining means 104 stored in the main controller MC determines the moving attitude or the imaging attitude.

The image reading device 5 reads image information from IP in which X-ray image information is stored. The image reading device 5 is stored in the main body portion 1, and the main body portion 1 is provided with a cassette insertion port 51 for inserting a cassette into the image reading device 5. Upon insertion of the cassette, the image reading device 5 starts to read image information. The image reading device 5 extracts IP from the inserted cassette, and after image information is read out from IP, the image reading device 5 erases the remaining image information in IP for which the reading has been finished. In the main controller MC is stored reading control means 105 for allowing or prohibiting reading of the image reading device 5. When the reading control means 105 prohibits reading, the image reading device 5 cannot read the image information. Furthermore, a cassette detecting sensor 53 for detecting insertion of a cassette is secured to the image reading device 5, and reading execution determining means 106 stored in the main controller MC determines whether the image reading device 5 executes reading.

A lid (shielding member) 52 which opens and closes is secured to the cassette insertion port 51. Under an open state of the lid 52, insertion of the cassette is possible, and under a close state of the lid 52, insertion of the cassette is impossible. The opening/closing of the lid 52 is executed by opening/closing control means 107 stored in the main controller MC. In this case, the lid is used as a shielding member for preventing insertion of the cassette. However, the shielding member is not limited to the lid, and a freely forward/backward movable projection may be used. For example, in the case where the freely forward/backward movable projection is used, when it enters the cassette insertion port, apart of the insertion port may be closed to make the insertion of a cassette impossible. When it backs away from the cassette insertion port, the insertion of the cassette may be made possible.

The image information read out by the image reading device 5 is stored in a storage device (not shown) through the main controller. The main controller generates an X-ray image from the image information read out from the image reading device 5 and displays the X-ray image on the monitor 14. On the monitor 14 are displayed patient information, examination information, etc. obtained from the X-ray generator 4, the setting display of the image reading device 5 and RIS (Radiology Information System). Furthermore, a touch panel is fixed to the monitor 14, whereby settings of the X-ray generator 4 and the image reading device 5, patient information, etc. can be input. First display control means 108a and second display control means 108b for making an X-ray image be displayed or non-displayed are stored in the main controller MC, and when the first display control means 108a or the second display control means 108b makes the X-ray image be non-displayed, no X-ray image is displayed on the monitor 14.

An embodiment using the mobile X-ray apparatus M will be described below. In the mobile X-ray apparatus M, when the brake control means 101 releases the electromagnetic brake 24 in the main controller MC, the reading control means 105 prohibits reading of the image reading device 5.

Example 1-1

There will be described a case where the reading operation of the image reading device 5 is executed when the operator manipulates the handle 12 to move the mobile X-ray apparatus M.

When the mobile X-ray apparatus M is moved, the brake control means 101 releases the electromagnetic brake 24, and even when a cassette is inserted in the image reading device 5, the reading control means 105 prohibits the reading of the image reading device 5, so that the image reading device 5 cannot execute the reading of the image information. When the brake control means 101 actuates the electromagnetic brake 24, the reading control means 105 permits the reading of the image reading device 5, whereby the image reading device 5 reads the image information when the mobile X-ray apparatus M is stopped.

As described above, the mobile X-ray apparatus M prohibits the reading of the image information when it is being moved. In other words, the mobile X-ray apparatus M makes the image information be read when it is stopped, whereby there can be reduced a risk that image information being read from IP is damaged due to vibration or impact. Furthermore, the reading of the image information is prohibited during movement, whereby there can be reduced a risk that IP being read is brought into contact with various kinds of parts in the image reading device due to vibration or impact, and thus damaged.

The image reading device 5 used in this embodiment is configured so that reading of image information is started upon insertion of a cassette. However, the effect of the present invention can be attained even when an image reading device in which reading is started upon start operation of the reading after a cassette is inserted.

Furthermore, the image reading device 5 is configured so that remaining image information is erased for IP for which image reading is finished. Therefore, the reading control means 105 prohibits the reading of image information, and also prohibits erasure of image information, whereby occurrence of omission of erasure due to vibration or impact can be suppressed. The same is applied to the following embodiment 3-1.

Example 1-2

There will be described a case where the operator executes a reading operation of the image reading device 5 when the mobile X-ray apparatus M is moved as in the case of the example 1-1. In the example 1-2, when the reading control means 105 prohibits the reading of the image reading device 5 in the main controller MC, the opening/closing control means 107 closes the lid 52 to prevent insertion of a cassette.

As described in the example 1-1, when the mobile X-ray apparatus M is moved, the reading control means 105 prohibits the reading of the image reading device 5. At this time, even when a cassette is tried to be inserted into the image reading device 5, the opening/closing control means 107 closes the lid 52 at the cassette insertion port 51 to prevent the insertion of the cassette. Therefore, the image reading device 5 cannot execute the reading of the image information.

According to the example 1-2, even when the operator tries to insert a cassette into the image reading device 5, it is impossible to insert the cassette during movement, and thus the reading operation of the image reading device 5 can be surely prevented during movement. Furthermore, it is impossible to insert a cassette into the image reading device 5 during movement, and thus IP can be prevented from coming into contact with various kinds of parts in the reading device due to vibration or impact and being damaged.

Example 2

There will be described a case where the operator executes an irradiation operation of X-ray from the X-ray generator 4 when the image reading device 5 executes reading of image information. In the example 2, when the determination result of the reading execution determining means 106 indicates that reading is being executed in the main controller MC, the irradiation control means 102 prohibits X-ray irradiation.

When a cassette is inserted in the image reading device 5 and reading of image information is started and executed, the reading execution determining means 106 determines that reading is being executed. At this time, even when it is tried to emit X-ray from the X-ray generator 4, the irradiation control means 102 prohibits X-ray emission, and thus no X-ray is emitted from the X-ray irradiation portion 4.

According to the example 2, when the image reading device 5 reads out image information, no X-ray is emitted from the X-ray generator 4. Therefore, image information which is being stored in IP under reading can be prevented from being damaged by an effect of leakage X-ray.

Example 3-1

There will be described a case where the reading operation of the image reading device 5 is executed when the operator executes the rotating operation of the support pole 31 or the up/down movement operation of the arm 32 to adjust the position of the X-ray generator 4. In the example 3-1, when the support mechanism control means 103 releases both the electromagnetic brakes 33 and 34 in the main controller MC, the reading control means 105 prohibits the reading of the image reading device 5.

When the operator executes the rotating operation of the support pole 31 or the up/down movement operation of the arm 32, the support mechanism control means 103 releases the electromagnetic brakes 33 and 34. At this time, even when a cassette is inserted in the image reading device 5, the reading control means 105 prohibits the reading of the image reading device 5. Therefore, the image reading device 5 cannot execute the reading of image information.

According to this example 3-1, when the support pole 31 is rotated or the arm 32 is moved upward and downward, no image information is read out. Therefore, there can be reduced the risk that image information being read from IP is damaged due to vibration or impact.

Example 3-2

In the Example 3-2, in addition to the construction described with reference to the example 3-1, in the main controller MC, when the determination result of the reading execution determining means 106 is being read, the support mechanism control means 103 actuates both the electromagnetic brakes 33 and 34 to prevent up/down movement of the arm and the rotation of the support pole.

When a cassette is inserted in the image reading device 5 and reading of image information is started and executed, the reading execution determining means 106 determines that the reading is being executed, and at this time even when the rotating operation of the support pole or the up/down movement operation of the arm is tried to be executed, the support mechanism control means 103 actuates the electromagnetic brakes 33 and 34, so that the rotational angle of the support pole 31 and the up/down movement position of the arm 32 are fixed.

According to the example 3-2, when the image reading device 5 reads image information, neither the support 31 is rotated, nor the arm 32 is moved upward and downward, and thus image information being read from IP can be prevented from being damaged due to vibration or impact.

Furthermore, there is a case where large rush current flows and static electricity occurs when the electromagnetic brakes are released, and particularly when the image reading device 5 is stored at the front side (at the support pole 31 side) of the main body portion 1, image information stored in IP inserted in the image reading device 5 may be damaged by the effect of the static electricity. However, according to the example 3-2, when a cassette is inserted in the image reading device 5 and reading of image information is started and executed, the respective electromagnetic brakes 33 and 34 are not released, and thus there can be reduced the risk that image information stored in IP being read is damaged by static electricity.

Furthermore, in order to prevent the damage of IP at maximum, when the reading control means 105 prohibits the reading, it is preferable that the opening/closing control means 107 closes the lid 52 of the cassette insertion port 51 to prevent insertion of the cassette.

Example 4-1

There will be described a case where the operator moves (moves) the mobile X-ray apparatus M under the state that an X-ray image is displayed on the monitor 14. According to the example 4-1, in the main controller MC, when the brake control means 101 releases the electromagnetic brake 24, the first display control means 108a sets the X-ray image to non-display.

When the mobile X-ray apparatus M is moved, the electromagnetic brake 24 is released by the brake control means 101. At this time, the X-ray image is switched to non-display by the first display control means 108a, and the X-ray image being displayed on the monitor 14 is set to the non-display state.

According to the example 4-1, when the mobile X-ray apparatus M is moved, no X-ray image is displayed on the monitor 14, and thus the risk that personal information is leaked during movement can be reduced.

Example 4-2

There will be described a case where the operator moves the mobile X-ray apparatus M under the state that the mobile X-ray apparatus M is switched to the moving attitude. In the example 4-2, in the main controller MC, when the determination result of the attitude determining means 104 indicates the moving attitude, the second display control means 108b sets the X-ray image to non-display.

After the imaging is finished, the mobile X-ray apparatus M is switched from the imaging attitude to the moving attitude, whereby the X-ray generator 4 is set to be stored at the upper portion of the mobile dolly 2. Therefore, the mobile X-ray apparatus M is easily moved (see FIG. 3). When the attitude determining means 104 determines the moving attitude, the X-ray image is switched to non-display by the second display control means 108b, and the X-ray image being displayed on the monitor 14 is not displayed.

According to the example 4-2, when the mobile X-ray apparatus M keeps its moving attitude, the X-ray image is not displayed on the monitor 14 irrespective of movement of the mobile X-ray apparatus M. For example, even when there occurs a situation that the operator is far away from the mobile X-ray apparatus M during movement, there is no concern that another person peeps at the X-ray image, and thus personal information can be surely prevented from leaking during movement.

Furthermore, when the X-ray image is set to non-display, only the X-ray image may be set to non-display, or patient information, etc. which are displayed simultaneously with the X-ray image may be set to non-display. Furthermore, it is preferable that the setting screen for the X-ray generator 4, etc. is allowed to be displayed so that next imaging can be prepared during movement.

As described with reference to the examples 4-1, 4-2, the technical idea that the x-ray image is not displayed on the monitor by using the first display control means or the second display control means when the mobile X-ray apparatus is moved is applicable to the general mobile X-ray apparatus having an X-ray image output portion for emitting X-ray from the X-ray generator and outputting X-ray transmitted through an imaging target as image information. For example, in addition to the mobile X-ray apparatus which can display an X-ray image picked up by using IP and the image reading device as in the case of the present invention, the technical idea may be also diverted to a mobile X-ray apparatus which can display an X-ray image picked up by using FPD (Flat Panel Detector).

As described above, the examples of the present invention are mere examples, and the present invention is not limited to the above embodiment. Various modifications may be possible within the scope not departing from the subject matter of the present invention. For example, a manual type mobile X-ray apparatus in which a mobile dolly has no driving wheel may be used.

A preferable embodiment of the present invention is configured to have a cassette insertion port for inserting a cassette having IP mounted therein into the image reading device, a shielding member for preventing insertion of a cassette by closing at least a part of the cassette insertion port, and opening/closing control means for preventing insertion of a cassette by closing the shielding member when the reading control means prohibits reading.

According to this construction, it is impossible to insert a cassette into the image reading device when the mobile X-ray apparatus runs, and thus the reading of the image reading device can be surely prohibited.

A preferable embodiment of the present invention is configured so that the mobile dolly has a driving wheel driven by a motor.

According to this construction, the movement of the mobile X-ray apparatus is easy and the labor of the operator can be reduced.

In general, there is a case where the distance between the X-ray generator and the image reading device is short and the irradiation amount of X-ray is set to be high for imaging in a hospital room or the like in the mobile X-ray apparatus. Therefore, when the image reading device reads image information, upon emission of X-ray from the X-ray generator, IP inserted in the image reading device detects X-ray leaking from the X-ray generator, and image information stored in IP may be damaged.

Therefore, the device of this invention may be equipped with reading execution determining means for determining whether the image reading device executes reading or not, and irradiation control means for prohibiting X-ray irradiation of the X-ray generator when the determination result of the reading execution determining means is executing the reading.

According to this construction, when the image reading device reads image information, no X-ray is emitted from the X-ray generator, and thus the risk that the image information stored in IP under reading is damaged can be reduced.

Furthermore, when imaging is executed in a hospital room or the like, the arrangement of the mobile X-ray apparatus is physically restricted due to the arrangement of beds or a surrounding environment in some cases, and it is desired to easily handle the X-ray generator.

Therefore, the device of this invention is preferably configured so that the device is secured to the support pole so as to be freely moved upward and downward and has an arm having the X-ray generator mounted at the tip portion thereof and a rotating mechanism which is freely rotatable around the support pole.

However, when the support pole is rotated or the arm is moved upward and downward under the state that the image reading device reads image information, the read-out image information may be damaged due to vibration or impact caused by the above operation.

Therefore, the device of this invention which makes it easy to handle the X-ray generator may be equipped with an electromagnetic brake for braking the up/down movement of the arm, an electromagnetic brake for braking the rotation of the support pole, and support mechanism control means for actuating or releasing these electromagnetic brakes. When the support mechanism control means releases both the electromagnetic brakes, the reading control means may prohibit reading.

According to this construction, when the up/down movement operation of the arm and the rotating operation of the support pole is executed, the image reading device cannot read image information, and thus the risk that the read-out image information is damaged by vibration or impact can be reduced.

Furthermore, it is preferable that reading execution determining means for determining whether the image reading device executes reading or not is provided and when the determination result of the reading execution determining means is executing reading, the support mechanism control means actuates both the electromagnetic brakes and prevents the up/down movement of the arm and the rotation of the support pole.

According to this construction, when the image reading device reads image information, it is impossible to execute the up/down movement operation of the arm and the rotating operation of the support pole, and the risk that the read-out image is damaged by vibration or impact can be reduced more greatly.

Furthermore, concern about personal information protection has been recently enhanced. For example, when an X-ray image of a patient is kept to be displayed on the display (monitor) under the state that the mobile X-ray apparatus is moved from a hospital room to another hospital room, this is not preferable because there is a risk that others know the personal information of the patient.

Therefore, the device of this invention may be equipped with a monitor for displaying an X-ray image generated from image information read out by the image reading device, and first display control means for setting the X-ray image to non-display when the brake control means releases the brake.

According to this construction, when the mobile X-ray apparatus runs, no X-ray image is displayed on the monitor, and thus the risk that personal information leaks can be reduced.

Furthermore, the device of this invention which makes it easy to handle the X-ray generator may be equipped with attitude determining means for determining a running attitude under which the X-ray generator is located at the upper portion of the mobile dolly and an imaging attitude under which the X-ray generator protrudes from the mobile dolly, a monitor for displaying an X-ray image generated from image information read out by the image reading device, and second display control means for setting the X-ray image to non-display when the determination result of the attitude determining means indicates the running attitude.

According to this construction, when the mobile X-ray apparatus keeps the running attitude, no X-ray image is displayed on the monitor irrespective of running of the mobile X-ray apparatus, and the risk that personal information leaks can be reduced more greatly. For example, even when there occurs a situation that the operator is far away from the mobile X-ray apparatus during movement, there is no concern that others peek at an X-ray image.

INDUSTRIAL APPLICABILITY

The mobile X-ray apparatus according to the present invention is preferably usable for a mobile X-ray apparatus for doctor's round visits.

The invention claimed is:

1. A mobile X-ray apparatus comprising:
a main body portion, a mobile dolly on which the main body portion is mounted;
a support pole that is erectly provided on the mobile dolly;
an X-ray generator supported on the support pole;
an image reading device for reading image information from an imaging plate in which X-ray image information is stored, characterized by further comprising:
detecting means for detecting whether the mobile dolly is being moved, and reading control means for prohibiting reading of the image reading device when it is detected by the detecting means that the mobile dolly is being moved;
reading execution determining means for determining whether the image reading device executes reading; and
irradiation control means for prohibiting irradiation of X-ray from the X-ray generator when a determination result of the reading execution determining means indicates that reading is being executed.

2. The mobile X-ray apparatus according to claim 1, wherein the mobile dolly has a driving wheel driven by a motor.

3. A mobile X-ray apparatus comprising:
a main body portion, a mobile dolly on which the main body portion is mounted;
a support pole that is erectly provided on the mobile dolly, an X-ray generator supported on the support pole;
an image reading device for reading image information from an imaging plate in which X-ray image information is stored, characterized by further comprising:
detecting means for detecting whether the mobile dolly is being moved, and reading control means for prohibiting reading of the image reading device when it is detected by the detecting means that the mobile dolly is being moved;
a cassette insertion port for inserting a cassette having an imaging plate mounted therein into the image reading device;
a shielding member for preventing insertion of a cassette by closing at least a part of the cassette insertion port; and
opening/closing control means for preventing insertion of a cassette by closing the shielding member when the reading control means prohibits reading.

4. A mobile X-ray apparatus comprising:
a main body portion, a mobile dolly on which the main body portion is mounted;
a support pole that is erectly provided on the mobile dolly, an X-ray generator supported on the support pole;
an image reading device for reading image information from an imaging plate in which X-ray image information is stored, characterized by further comprising:
detecting means for detecting whether the mobile dolly is being moved, and reading control means for prohibiting reading of the image reading device when it is detected by the detecting means that the mobile dolly is being moved;
an arm that is secured to the support pole so as to be freely moved upward and downward and has the X-ray generator at a tip portion thereof;
a rotating mechanism that is freely rotatable centering around the support pole; and
an up/down movement detector for detecting up/down movement of the arm and a rotation detector for detecting rotation of the support pole, wherein the reading control means prohibits reading when the up/down movement detector or the rotation detector detects up/down movement or rotation.

5. A mobile X-ray apparatus comprising:
a main body portion, a mobile dolly on which the main body portion is mounted;
a support pole that is erectly provided on the mobile dolly, an X-ray generator supported on the support pole;
an image reading device for reading image information from an imaging plate in which X-ray image information is stored, characterized by further comprising:
detecting means for detecting whether the mobile dolly is being moved, and reading control means for prohibiting reading of the image reading device when it is detected by the detecting means that the mobile dolly is being moved;
a monitor for displaying an X-ray image generated from image information read out by the image reading device; and
first display control means for setting the X-ray image to non-display when the detecting means detects a movement state.

6. A mobile X-ray apparatus comprising:
a main body portion, a mobile dolly on which the main body portion is mounted;
a support pole that is erectly provided on the mobile dolly, an X-ray generator supported on the support pole;
an image reading device for reading image information from an imaging plate in which X-ray image information is stored, characterized by further comprising:
detecting means for detecting whether the mobile dolly is being moved, and reading control means for prohibiting reading of the image reading device when it is detected by the detecting means that the mobile dolly is being moved;
an arm that is secured to the support pole so as to be freely moved upward and downward and has the X-ray generator at a tip portion thereof;
a rotating mechanism that is freely rotatable centering around the support pole;
attitude determining means for determining a moving attitude at which the X-ray generator is located at an upper portion of the mobile dolly and an imaging attitude at which the X-ray generator protrudes from the mobile dolly;
a monitor for displaying an X-ray image generated from image information read out by the image reading device; and
second display control means for setting the X-ray image to non-display when a determination result of the attitude determining means indicates a moving attitude.

* * * * *